United States Patent [19]

Batcho et al.

[11] 4,137,404

[45] Jan. 30, 1979

[54] SYNTHESIS OF TRYPTOPHANS

[75] Inventors: Andrew D. Batcho, North Caldwell; Willy Leimgruber, Montclair, both of N.J.

[73] Assignee: Hoffmann-La Roche Inc., Nutley, N.J.

[21] Appl. No.: 862,304

[22] Filed: Dec. 20, 1977

[51] Int. Cl.² ........................................... C07D 263/18
[52] U.S. Cl. .................................... 542/442; 542/421; 542/443; 260/326.14 T; 260/345.7 R
[58] Field of Search .................... 542/442; 260/307 A

[56] References Cited

U.S. PATENT DOCUMENTS

| | | | |
|---|---|---|---|
| 3,949,000 | 4/1976 | Violet | 260/606.5 P |
| 3,956,304 | 5/1976 | Schwarze et al. | 260/307 A |
| 4,073,795 | 2/1978 | Batcho et al. | 260/326.14 T |

OTHER PUBLICATIONS

Steglich et al., Chem. Bericht 101 (1968), pp. 308-322.
Ellinger et al., Chem., Ber. 40 (1907), pp. 3029-3034.
Cooley et al., J. Biol. Chem. 185 (1950), p. 287.
Shaw et al., J. Org. Chem. 23 (1958), p. 1171.
Kaneko et al., Nippon Kag. Zasshi 79 (1958), p. 91.
Coppola et al., Heterocycl. Chem. 11 (1974), p. 51.
Sawada et al., Bulletin Kyoto U. Ed. 47 (1975), p. 19.
Ali et al., Chem. Abstracts 85 #47026.

*Primary Examiner*—Arthur P. Demers
*Attorney, Agent, or Firm*—Jon S. Saxe; Bernard S. Leon; George W. Johnston

[57] ABSTRACT

A process is disclosed for preparing racemic and optically pure tryptophans through novel intermediates.

3 Claims, No Drawings

SYNTHESIS OF TRYPTOPHANS

BACKGROUND OF THE INVENTION

Tryptophan, α-amino-β-indolepropionic acid is an amino acid originally isolated from enzymatic digests of proteins. Various tryptophan compounds can be obtained by extraction, fermentation or chemical synthesis. Extraction is a difficult process because tryptophan is easily destroyed during acid hydrolysis of proteins, and racemization occurs on alkaline hydrolysis. Fermentative methods include the production of tryptophan from anthranilic acid or indoles. The chemical synthetic methods are generally of two types: (1) syntheses in which an alanyl residue is added to a preformed indole and (2) syntheses in which the indole portion of the molecule is formed late in the sequence. The latter chemical syntheses are preferred because the preformed indoles of the former chemical syntheses are costly raw materials. Furthermore, the latter chemical syntheses involve a minimum of conversion during which the chemically sensitive indole nucleus might be destroyed. However, the latter chemical routes are not ideal because the required indole formation usually involves cyclization into an aromatic ring which leads to undesirable mixtures of isomers. The formation of isomers is particularly acute in the case of 4- and 6-substituted tryptophans.

The instant invention provides a means for the obtention, in high yield, of racemic and optically pure tryptophans, the D-enantiomers of which have potential value as non-nutritive sweeters.

Numerous substances have been proposed and/or used as non-nutritive sweetening agents, affording the consumer ingesting the same a sense of sweetness at least desirably comparable to that obtained with natural sugar, but without caloric effect. Such substances are necessary for some persons in order to limit intake of the natural sugars and thereby to control various health conditions, including diabetes. Many of these substances, however, have severe disadvantages. The most frequently encountered disadvantages are a bitter aftertaste and toxic side effects at rates not substantially different from those at which the sweetening effect is obtained. Only two classes of non-nutritive sweetening substances are used to any extent: saccharin-type compounds and cyclamate-type compounds. Both classes have the typical disadvantage of a bitter aftertaste; and in addition, cyclamate-type compounds have only limited activity.

Among the various categories of chemicals which have been evaluated for sweetening effect are the amino acids. A recent publication, Vuataz et al., Experientia, Vol. XXI, pages 692–694, inclusive (1965), reports the evaluation of a number of amino acids, the enantiomorphs being evaluated separately where available. The report shows that while a number of amino acids are sweet in the D form, this is not an absolute correlation. Furthermore, despite the sweet taste of the D-enantiomorph of a given amino acid, the L-enantiomorph of the same amino acid may be bitter. Resolution of the two enantiomorphs of a given amino acid is often difficult. For these various reasons, despite the contribution of Vuataz et al., no amino acid is being used in the sweetening art.

Moreover, throughout the sweetening art, it is well known that there is no correlation between structure and activity, as even relatively small changes in chemical structure often destroy activity.

In recent years the commercially-available synthetic sweetners, saccharin and cyclamate, have encountered some difficulties in toxicological studies. Aftertaste problems have also plagued these products. It has been evident, therefore, that a need exists for new sweetening agents. This need has been met, in part, by the new sweetener 1-aspartyl-1-phenylalanine methyl ester (Aspartame ®), but this dipeptide ester has shown instability under some conditions.

It has recently been discovered that certain substituted tryptophan compounds in their D form exhibit a sweet taste of a marked degree. See U.S. Pat. No. 3,899,592 to Suarez et al. and U.S. Pat. application Ser. No. 698,573 to Batcho et al., filed June 22, 1976. Substituted D tryptophans thus are important as artifical sweetners.

Additionally, because tryptophan in the L form is an essential amino acid, it has importance as a food supplement.

According to the present invention, tryptophans (unsubstituted or substituted) of the D or L forms are prepared by novel processes via novel intermediates which avoid the above described difficulties of the prior art processes.

SUMMARY OF THE INVENTION

Compounds of the formulae:

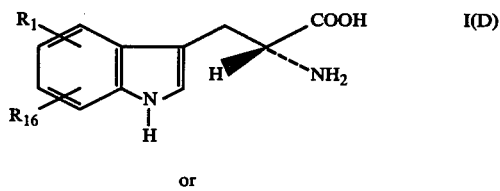   I(D)

or

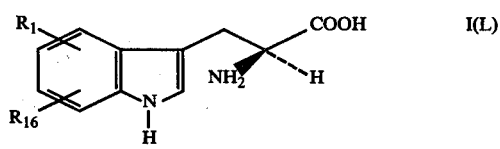   I(L)

are prepared by treating compounds of the formula

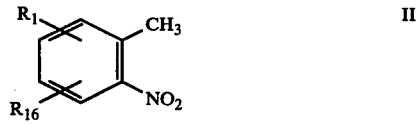   II wherein $R_1$ and $R_{16}$ are halogen, lower alkyl, hydroxy, lower alkoxy, aralkyloxy, amino, trihalomethyl or hydrogen;

in accordance with the following scheme;

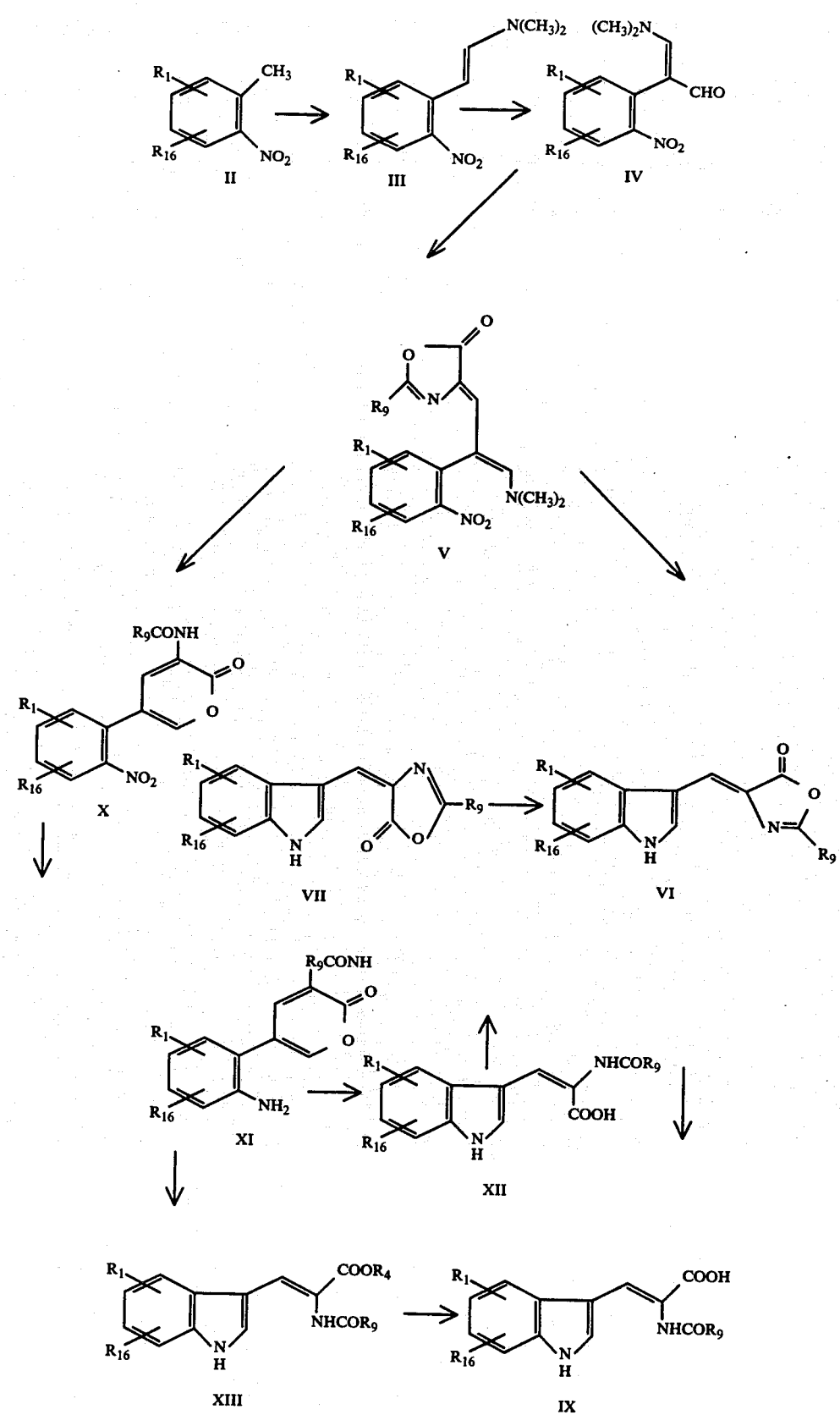

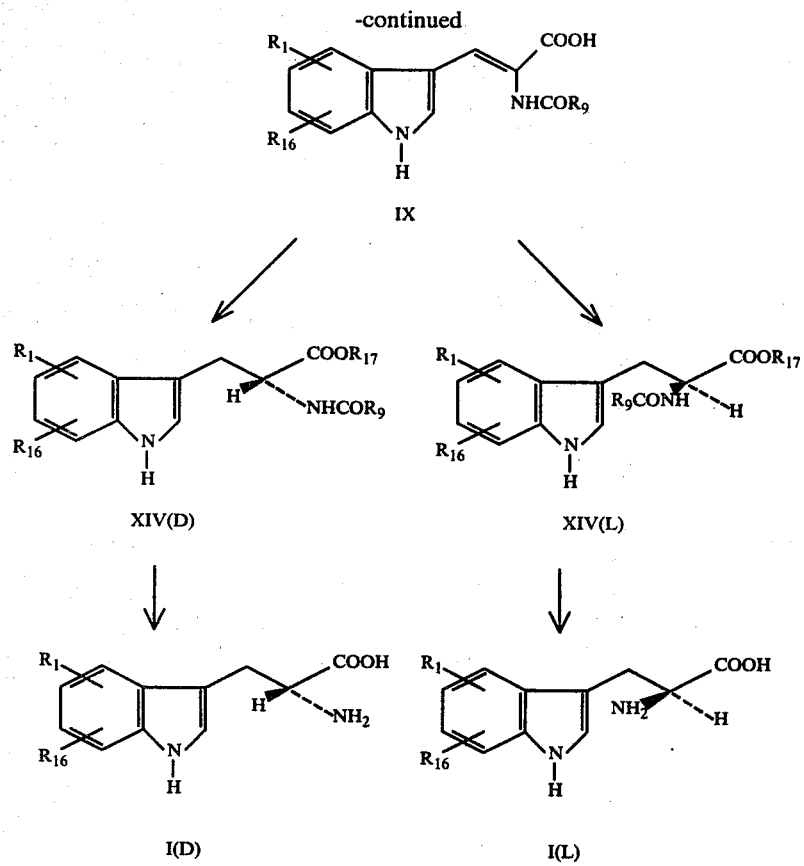

wherein $R_1$ and $R_{16}$ are as above; $R_4$ is lower alkyl, aryl or aralkyl; $R_9$ is lower alkyl, aryl, hydrogen or halo-lower alkyl; and $R_{17}$ is hydrogen, ammonium or lower alkyl ammonium.

DETAILED DESCRIPTION OF THE INVENTION

The term "alkyl" as used herein, connotes straight or branched chain saturated hydrocarbon groups containing 1 to 20 carbon atoms. The term "lower alkyl" connotes the above hydrocarbon groups containing 1–6 carbon atoms. Typical lower alkyl groups are methyl, ethyl, propyl, isopropyl and the like. The term "halogen" connotes all four halogens (i.e., chlorine, bromine, fluorine and iodine). The term "lower alkylene" denotes alkylene groups of 2–6 carbon atoms such as ethylene, propylene, butylene and the like. The term "lower alkanol" connotes alkanols having 1–6 carbon atoms such as methanol and propanol. The term "lower alkoxy" connotes alkoxy groups having 1 to 6 carbon atoms such as methoxy and ethoxy. The term "acyl" connotes alkanoyl groups derived from aliphatic carboxylic acids, preferably lower alkanoic acids containing from 1–6 carbon atoms (e.g., acetic acid, propanoic acid, butyric acid, etc.) as well as aroic acids (e.g., benzoic acid). The term "lower alkyl amino" connotes mono-, di-, or tri-lower alkyl substituted amines. Typical lower alkyl amino groups are methylamino, ethylamino, diethylamino and the like. The term "aryl" connotes mono-nuclear aryl groups such as unsubstituted and substituted phenyl. The substitutions are located in one or more positions and selected from halogen, lower alkyl, lower alkoxy, nitroamino and lower alkylamino. The term "alkali metal" as used in this specification includes any one of the alkali metals such as lithium, sodium, potassium, rubidium and caesium. The term "alkaline earth metals" includes any of the conventional alkali earth metals such as calcium. In this application, a solid tapering line (▶) indicates a substituent above the plane of the paper and a dashed line (---) indicates a substituent below the plane of the paper.

Compounds I(D), I(L), through XIV(D), XIV(L), will be discussed hereinbelow and have the formula described in the Summary of the Invention of the present application.

In accordance with the present invention, compound II is treated with a formamide acetal to form compound III. The procedure for forming compound III from compound II is described in U.S. Pat. No. 3,732,245 and U.S. application Ser. No. 698,573, now Pat. No. 4,073,795, both to Batcho et al.

Compound III is treated with an acid halide and dialkylformamide to form compound IV. The procedure for forming compound IV from compound III is described in U.S. Pat. application Ser. No. 698,573 to Batcho et al. In carrying out this reaction any of the conditions of Vilsmeier formylation may be employed.

Compound IV is reacted with N-acyl derivatives of glycine or α-aminomalonic acid in the presence of a catalytic amount of base and a dehydrating agent to form compound V.

In carrying out this reaction, N-acyl derivatives of glycine or α-aminomalonic acid may be employed. Particular derivatives useful in this procedure include acetyl or aroylamides of glycine such as N-acetylglycine and N-benzoylglycine, and N-acyl-α-aminomalonic acids such as acetamidomalonic acid. N-acetylglycine is preferred when tryptophan or alkyltryptophans are the ultimately desired products.

Any conventional dehydrating agent can be utilized in the conversion of compound III to compound IV. In some cases the dehydrating agent may also act as a solvent. Acid anhydrides such as acetic anhydride are such dehydrating agents.

As the catalyst, any conventional inorganic or organic bases may be employed. Illustratively, the base catalyst is selected from salts of inert acids such as sodium acetate, potassium acetate, sodium carbonate, potassium carbonate and lead acetate; inert tertiary amines such as trialkylamine and pyridine; and alkali metal and alkaline earth metal oxides such as magnesium oxide.

In carrying out this reaction, any of the conditions conventional to an Erlenmeyer azlactone synthesis may be utilized.

According to one aspect of the present invention, compound V may be catalytically or chemically reduced to compound VI, which is the Z isomer.

In carrying out this reduction, any conventional means and catalysts for selectively catalytically reducing a nitro group may be employed. Typical reduction catalysts are the oxides of chromium, molybdenum, tungsten, platinum, palladium, rhodium, cobalt, nickel and ruthenium. Platinum is preferred. While this reaction is generally carried out at temperatures and hydrogen pressures of $-10°$ C. to $100°$ C. and 1 to 200 atmospheres, the catalytic reduction preferably proceeds at $20°$ C. to $30°$ C. and 1 to 5 atmospheres.

Alternatively, compound V may be reduced to compound VI by any convention means for chemically reducing a nitro group to an amino group. For example, conventional reducing agents may be employed. Among the preferred reducing agents are zinc dust and iron dust. While this reaction is generally carried out at $-10°$ C. to $100°$ C., $10°$ C. to $30°$ C. is preferred.

To improve the desired yield of compound VI, compound V may be chemically reduced in the presence of an organic acid (e.g., acetic acid) and an acid anhydride, such as acetic anhydride.

The catalytic or chemical reduction may occur in the presence of any conventional solvent including hydrocarbons such as benzene and toluene; ethyl acetate; acetic acid; acetic anhydride; dioxane, dimethylformamide; or tetrahydrofuran.

In certain cases, particularly with the chemical reduction of compound V, compound VII, which is the E isomer, is formed as a side product. To increase the amount of desired compound VI, the reaction product containing compounds VI and VII may be equilibrated. Any conventional means for equilibrating $\alpha,\beta$-unsaturated azlactone may be employed. C.

In accordance with the preferred embodiment of the present invention, the equilibration is carried out with any inert tertiary amine base preferably trimethylamine, triethylamine and pyridine. Although the temperature for carrying out the equilibration is not critical, the approximate temperature range for this equilibration of compound VII to compound VI is $-10°$ C, to $150°$ C., preferably $40°$ C. to $90°$ C.

Compound VI is then hydrolyzed under aqueous conditions either in the presence of an acid or base to compound IX. Acid hydrolysis is preferred.

The hydrolysis of compound VI to compound IX may utilize any conventional aqueous solutions of any conventional mineral or organic acids. Suitable mineral acids include hydrofluoric acid, hydrochloric acid and sulfuric acid. Typical organic acids are lower alkanoic acids such as acetic acid, propanoic acid and benzoic acid. Acetic acid is preferred. Although not required, any conventional solvent useful in hydrolysis may be employed in this reaction. While this hydrolysis is generally carried out at a temperature from $-10°$ C. to $50°$ C., $20°$ C. to $30°$ C. is preferred.

Alternatively, compound VI may be hydrolyzed under conventional basic and aqueous conditions to the compound IX. Any conventional method of basic hydrolysis under aqueous conditions can be utilized. Among the suitable bases are alkali metals, alkaline earth metal hydroxides and carbonates; and tertiary amines. Dilute sodium hydroxide is a preferred base. After the completion of the above basic hydrolysis, the free acid can be recovered by adjusting the pH. Any conventional method of lowering the pH of a basic medium may be employed. For example, a mineral acid may be added to the medium. Although the temperature of the basic reaction is not critical, room temperature is preferred.

In accordance with the procedure described by U.S. Pat. application Ser. No. 698,573 to Batcho et al., compound IX can be converted to either XIV(D) (the D isomer) or XIV(L) (the L isomer).

As further described in U.S. Pat. application Ser. No. 698,573, compound XIV(D) or compound XIV(L) can be converted into the desired tryptophan, compound (I)D (the D isomer) or compound I(L) (the L isomer), respectively.

According to another aspect of the present invention, compound V is hydrolytically converted in an aqueous medium and in the presence of an organic acid or a weak mineral acid to compound X.

In carrying out this conversion, any conventional organic acid or weak mineral acids in an aqueous medium may be utilized. To increase the yield of compound X, any conventional weak organic acids may be employed. Among the preferred weak organic acids are lower alkanoic acids containing from 2 to 6 carbon atoms (e.g., acetic acid, propanoic acid and benzoic acid). Although not required, the reaction may proceed in any conventional inert organic solvent. Typical solvents are ethers such as tetrahydrofuran, methyl ethyl ether, dioxane and diethyl ether; alkanones such as acetone and methyl ethyl ketone; and aromatic hydrocarbons such as benzene and toluene. The temperature for the acid hydrolysis is not critical but may occur approximately at 0 to $100°$ C., and preferably at 40 to $60°$ C.

In lieu of acid hydrolysis, compound V may be hydrolyzed under conventional basic conditions in a solvent medium. Suitable bases include alkali metal and alkaline earth metal hydroxides and tertiary organic amines, such as triethylamine and pyridine. Sodium hydroxide is preferred. With tertiary amines, the reaction preferably occurs in an aqueous medium. The reaction conditions and applicable solvents are the same as those described with regard to the above acid hydrolytic conversion. The base hydrolysis of compound V is then followed by adjusting the pH to produce compound X. Any conventional method of lowering the pH of a basic medium may be employed. For example, any conventional mineral acid may be utilized.

Compound X then is selectively reduced to compound XI. In carrying out this reduction, any conventional method for selectively reducing a nitro group to an amino group may be employed. For example, one may catalytically hydrogenate compound X to compound XI. Any conventional hydrogenation catalyst such as those mentioned hereinbefore can be utilized. This hydrogenation may be carried out under any conventional hydrogenation conditions. Additionally, any of the conventional inert solvents useful in catalytic hydrogenation may be employed. Suitable solvents are dimethylformamide, lower alkanols (e.g., methanol and ethanol), ether (e.g., dioxane and tetrahydrofuran) and aromatic hydrocarbons (e.g., benzene and toluene).

While this catalytic hydrogenation generally proceeds at −10° C. to 100° C., 15° C. to 30° C. is preferred.

Another suitable method to reduce compound X to compound XI employs utilizing any conventional reducing agent capable of converting a nitro group to an amino group. Suitable reducing agents include zinc dust and iron dust. To increase the yield of compound XI, the reducing agent may be utilized in the presence of a weak organic acid. Acetic acid is preferred. Although temperature is not critical for the chemical reduction, room temperature to 100° C. is preferred.

According to another aspect of the present invention, compound XI is hydrolyzed under aqueous conditions in the presence of acid or base to compound XII. Basic hydrolysis is preferred.

Any conventional method of basic hydrolysis under aqueous conditions may be employed. Suitable bases are alkali metal, alkaline earth metal hydroxides and carbonates, and tertiary organic amines such as pyridine. Sodium hydroxide is preferred. After the completion of the above hydrolysis under basic conditions, the free acid may be recovered by adjusting the pH.

In lieu of basic hydrolysis, any conventional mineral or organic acid under aqueous conditions may be utilized to hydrolyze compound XI to compound XII. Suitable acids and conditions have been described hereinbefore with regard to the conversion of compound VI to compound IX.

While the temperature for carrying out the acid or base hydrolysis of compound XI is generally −10° C. to 100° C., 15° C. to 30° C. is preferred.

Compound XII then can be converted to previously described compound IX via intermediates VII and VI.

Compound XII is initially converted to compound VII. In carrying out this reaction, any conventional dehydrating agents may be employed. Typical dehydrating agents are anhydrides of lower alkanoic acids such as acetic anhydride and propanoic anhydride. Acetic anhydride is preferred. Although the temperature is not critical, this conversion is preferably carried out at 50 to 60° C.

By the process described hereinbefore, compound VII then may be equilibrated to compound VI. The latter compound may be converted to the desired tryptophan of formula I(D) or I(L) via intermediate compounds IX and XIV(D) or XIV(L). The procedure for this conversion have been described previously.

Alternatively, compound XI may be converted to compound IX via compound XIII.

Compound XI may be converted to compound XIII by solvolysis in alcohols selected from the group of primary and secondary organic alcohols and in the presence of base under anhydrous conditions. In carrying out this reaction, any conventional primary or secondary organic alcohol may be employed. Typical alcohols include lower alkanols, preferably methanol and propanol; and aralkanols such as benzyl alcohol.

Any conventional inorganic or organic bases are acceptable. Typical bases are alkali and alkaline earth metal lower alkoxides and tertiary lower alkyl amines such as triethylamine.

Although not necessary, the lower alkanols also may be utilized as solvents. When methanol is selected as the solvent, sodium methylate is a preferred base.

While the temperature range for carrying out this conversion is not critical, 0° to 100° C. is suitable and room temperature is preferred.

Compound XIII may be converted to compound IX by conventional methods of hydrolyzing an ester to its acid. Such methods illustratively are described in U.S. patent application Ser. No. 698,573 to Batcho et al.

Compound IX then can be converted to the desired tryptophan of formula I(D) or I(L) by the processes described in U.S. Pat. application Ser. No. 698,573.

The following non-limiting examples illustrate the instant invention. All temperatures are in degrees Centigrade unless otherwise stated.

EXAMPLE 1

Preparation of 4-[3-dimethylamino-2-(4-methyl-2-nitrophenyl)-2-propen-1-ylidene]-2-methyl-2-oxazolin-5-one 148.6 g. (1.25 mol) of N-acetylglycine, 411.8 g. (5.0 mol) of anhydrous sodium acetate, and 117.6 g. (0.050 mol) of 3-dimethylamino-2-(4-methyl-2-nitrophenyl)-acrolein, and 2.5 l. of acetic anhydride were charged into a 5-liter 3-necked flask equipped with thermometer, stirrer, and nitrogen inlet. This mixture was stirred for 15 minutes, and 75 ml. (1.06 mol) of acetyl chloride was added dropwise thereto over about a 30 minute period. The temperature rose to 38° C., and the resulting mixture had a deep red color. After approximately 1 hour, the temperature of the mixture began to fall and an additional 75 ml. (1.06 mol) of acetyl chloride was added thereto over another 30 minute period. The temperature rose to 41° C. and the resulting mixture was stirred for 24 hours. After removing most of the acetic anhydride by vacuum distillation using a 60–70° C. water bath, about 2 l. of ice-water was added thereto. The resulting red suspension was stirred for 1 hour as it was brought to room temperature and was sequentially extracted with 2 l. of methylene chloride and 1 l. of methylene chloride. Both extracts were washed in a counter-current manner with 1 l. of water and 1 l. of 5% sodium bicarbonate and then dried over sodium sulfate, filtered, and evaporated to yield 162.1 g. of a dark red solid. Recrystallization from 600 ml. of methylene chloride and 400 ml. of hexane at 5° C. yielded (in 2 crops) 93.0 g. (59%) of 4-[3-dimethylamino-2-(4-methyl-2-nitrophenyl)-2-propen-1-ylidene]-2-methyl-2-oxazolin-5-one as a dark red solid (mp 200–201° C.). The analytical sample was recrystallized from ethyl acetate, mp 202.5–203.5° C.

EXAMPLE 2

Preparation of 4-[3-dimethylamino-2-(4-methyl-2-nitrophenyl)-2-propen-1-ylidene]-2-methyl-2-oxazolin-5-one.

1.8 g. of acetamidomalonic acid was added portionwise over a 5 minute period to a suspension of 2.34 g. (10 mmol) of 3-dimethylamino-2-(4-methyl-2-nitrophenyl)-acrolein, 20 ml. of acetic anhydride, and 1.6 ml. of pyridine cooled to −15° C. When the resulting mixture warmed to −8° C., the evolution of gas was observed. After 3 hours, the mixture attained room temperature. Since some starting material still remained, the reaction mixture was cooled to 5° C. and an additional 1.8 g. of acetaminomalonic acid were added thereto. Over a 16 hour period, the resulting mixture was allowed to come to room temperature, poured into 300 ml. of water, and adjusted to pH 8 with 100 ml. of 10% sodium bicarbonate. Two extractions with methylene chloride (500 ml. and 300 ml.), and a wash with 100 ml. of 10% sodium bicarbonate in a counter-current manner were followed by drying over sodium sulfate ($Na_2SO_4$) and evaporation in vacuo to yield 3.2 g. of a red solid. Recrystallization from 20 ml. of ethyl acetate afforded 2.45 g. (76%) of 4-[3-dimethylamino-2-(4-methyl-2-nitrophenyl)-2-propen-1-ylidene]-2-methyl-2-oxazolin-5-one as red needles, (mp 200–201° C.).

EXAMPLE 3

Preparation of
(Z)-α-acetamido-6-methylindole-3-acrylic acid from 4-[3-dimethylamino-2-(4-methyl-2-nitrophenyl)-2-propen-1-ylidene]-2-methyl-2-oxazolin-5-one A stirred slurry of 31.5 g. (100 mmol) of 4-[3-dimethylamino-2-(4-methyl-2-nitrophenyl)-2-propen-1-ylidene]-2-methyl-2-oxazolin-5-one in 350 ml. of acetic acid and 40 ml. (400 mmol) of acetic anhydride was prepared in a three-neck round bottom flask and maintained at 15–20° C. by an ice-water bath while 30.0 g. (460 mmol) of zinc dust were added in 3 g.-portions over 30 minutes. After stirring for 1 hour, 1 l. of ice-water (1:1 parts by volume) and 400 ml. of methylene chloride were added to the flask. After 15 minutes, the resulting three-phase system was filtered.

The two-phase filtrate was separated and the aqueous upper phase was washed with 500 ml. of methylene chloride. The methylene chloride phases were washed in counter-current manner with 1 l. of water. The extracts were combined and evaporated in vacuo to yield 20.4 g. of a yellow solid.

The filter cake was digested with 300 ml. of N,N-dimethylformamide and filtered. The residue consisted of 6.3 g. of unreacted zinc dust. The dimethylformamide solution was evaporated in vacuo to yield 3.4 g. of solid which was digested with 2 × 100 ml. of benzene. The benzene insoluble residue (2.0 g.) was discarded. The soluble fraction afforded, after the removal of the solvent in vacuo, 1.25 g. of a yellow solid which was combined with the yellow solid obtained from the methylene chloride extraction to yield a total of 21.6 g. (90%) of a 7:3 mixture of (Z) and (E)-4-(6-methylindol-3-ylmethylene)-2-methyl-2-oxazolin-5-one.

The 21.6 g. of (Z) and (E)-4-(6-methylindol-3-ylmethylene)-2-methyl-2-oxazolin-5-one was heated in 400 ml. of toluene and 10 ml. of triethylamine at 80° C. for 4 hours and then evaporated in vacuo to yield a crude product containing 90–95% of (Z)-4-(6-methylindol-3-ylmethylene)-2-methyl-2-oxazolin-5-one.

A suspension of the 21.6 g. of equilibrated crude azlactone (Z)-4-(6-methylindol-3-ylmethylene)-2-methyl-2-oxazolin-5-one in 200 ml. of 90% aqueous acetic acid was stirred at room temperature for 19 hours then cooled to 5° C. and filtered. The filter cake was washed with 300 ml. of water and dried at 60° C./1 mmHg for 48 hours to yield 20.08 g. (74%) of (Z)-α-acetamido-6-methylindole-3-acrylic acid as a yellow solid (mp 222–223°).

EXAMPLE 4

Preparation of
(Z)-4-(6-methylindol-3-ylmethylene)-2-methyl-2-oxazolin-5-one by Catalytic Reduction of 4-[3-dimethylamino-2-(4-methyl-2-nitrophenyl)-2-propen-1-ylidene]-2-methyl-2-oxazolin-5-one A 500-ml. Parr bottle was charged with 3.16 g. (10 mmol) of 4-[3-dimethylamino-2-(4-methyl-2-nitrophenyl)-2-propen-1-ylidene]-2-methyl-2-oxazolin-5-one, 95 ml. of acetic acid, 5 ml. of acetic anhydride, and 602 mg. of 10% palladium on charcoal. The resulting suspension was shaken under 3 atmospheres of hydrogen for 6 hours. The pressure drop corresponded to 41 mmol (part of which was due to the reduction of the acetic anhydride). The suspension was filtered through a bed of diatomaceous earth and the filter cake was washed several times with methylene chloride. The combined filtrates were poured into 400 ml. of water, extracted with 2 × 300 ml. of methylene chloride which were washed with 150 ml. of water. The combined methylene chloride phases were dried over sodium sulfate, filtered, and evaporated in vacuo to yield 1.5 g. of residue. Chromatography on 10 g. of silica gel afforded 150 mg. of (Z)-4-(6-methylindol-3-ylmethylene)-2-methyl-2-oxazolin-5-one (mp 189–191°).

EXAMPLE 5

Preparation of
(Z)-4-(6-methylindol-3-ylmethylene)-2-methyl-2-oxazolin-5-one by Catalytic Reduction of 4-[3-dimethylamino-2-(4-methyl-2-nitrophenyl)-2-propen-1-ylidene]-2-methyl-2-oxazolin-5-one A 500-ml. Parr bottle was charged with 3.17 g. (10 mmol) of 4-[3-dimethylamino-2-(4-methyl-2-nitrophenyl)-2-propen-1-ylidene]-2-methyl-2-oxazolin-5-one, 5 ml. of acetic anhydride, 95 ml. of glacial acetic acid, and 600 mg. of 10% platinum on charcoal, and was shaken under 3 atmospheres of hydrogen for 12 hours. During this time, 34 mmol of hydrogen were absorbed. The reaction was treated as in Example 4. 0.83 g. (35%) of (Z)-4-(6-methylindol-3-ylmethylene)-2-methyl-2-oxazolin-5-one (mp 194–196° C.) was thereby obtained.

EXAMPLE 6

Preparation of
(Z)-4-(6-methylindol-3-ylmethylene)-2-methyl-2-oxazolin-5-one by Catalytic Reduction of 4-[3-dimethylamino-2-(4-methyl-2-nitrophenyl)-2-propen-1-ylidene]-2-methyl-2-oxazolin-5-one A 500-ml. Parr bottle was charged with 9.46 g. (30 mmol) of 4-[3-dimethylamino-2-(4-methyl-2-nitrophenyl)-2-propen-1-ylidene]-2-methyl-2-oxazolin-5-one, 225 ml. of toluene, 15 ml. of acetic anhydride, and 1.0 g. of 10% platinum on charcoal. The resulting suspension was shaken under 3 atmospheres of hydrogen for 48 hours during which time approximately 100 mmol of hydrogen was absorbed. At 1.5 hours and 22 hours of the 48 hour period, additional 1.0 g. amounts of catalyst were added to the suspension. The resulting mixture was filtered through a bed of diatomaceous earth to remove the catalyst and the filter cake was washed several times with a total of 300 ml. of methylene chloride. The filtrate was concentrated in vacuo and applied to 200 g. of silica gel. Elution with methylene chloride followed by recrystallization from ethyl acetate afforded (in two crops) 2.32 g. (32%) of (Z)-4-

(6-methylindol-3-ylmethylene)-2-methyl-2-oxazolin-5-one (mp 199.5-201° C.).

The analytical sample was recrystallized from ethyl acetate-ether (mp 197.5-198.5° C.).

EXAMPLE 7

Equilibration of (E)-4-(6-methylindol-3-ylmethylene)-2-methyl-2-oxazolin-5-one

A solution of 94 mg. of (E)-4-(6-methylindol-3-ylmethylene)- 2-methyl-2-oxazolin-5-one in 0.1 ml. of triethylamine and 3 ml. of methylene chloride was heated at reflux under a nitrogen atmosphere for 2.5 hours. After evaporation in vacuo, the residue was taken up in 0.25 ml. of perdeuterodimethylsulfoxide. A 9:1 mixture of (Z)-4-(6-methylindol-3-ylmethylene)-2-methyl-2-oxazolin-5-one and its E isomer resulted.

EXAMPLE 8

Preparation of (Z)-α-acetamido-6-methylindole-3-acrylic acid from (Z)-4-(6-methylindol-3-ylmethylene)-2-methyl-2-oxazolin-5-one A suspension of 4.0 g. (16.7 mmol) of (Z)-4-(6-methylindol-3-ylmethylene)-2-methyl-2-oxazolin-5-one in 40 ml. of aqueous acetic acid (90%) was stirred overnight at room temperature, and then filtered to yield 3.91 g. (85%) of (Z)-α-acetamido-6-methylindole-3-acrylic acid as a yellow powder (mp 226.5-228.0° C.).

EXAMPLE 9

Preparation of 3-acetamido-5-(4-methyl-2-nitrophenyl)-2H-pyran-2-one from 4-[3-dimethylamino-2-(4-methyl-2-nitrophenyl)-2-propen-1-ylidene]-2-methyl-2-oxazolin-5-one 140 ml. of water followed dropwise by 154 ml. of 1.0 N sodium hydroxide were added over 15 minutes to a stirred solution of 22.0 g. (70 mmol) of 4-[3-dimethylamino-2-(4-methyl-2-nitrophenyl)-2-propen-1-ylidene]-2-methyl-2-oxazolin-5-one in 1 l. of acetone at 50° C. The resulting solution was allowed to cool to room temperature and after 1 hour the acetone was removed in vacuo. The remaining dark aqueous solution was cooled to 5° C. and 77 ml. of 2 N hydrochloric acid was added thereto. The resulting suspension was extracted with 2 × 1 l. of methylene chloride which were backwashed with 300 ml. of water in a countercurrent manner. The organic phases were combined, dried over sodium sulfate, filtered, and evaporated to yield 20.0 g. of crude product. Chromatography on silica gel, eluting with ethyl acetate-methylene chloride (1:4), yielded 10.57 g. (52%) of 3-acetamido-5-(4-methyl-2-nitrophenyl)-2H-pyran-2-one (mp 224-225° C.).

The analytical sample was recrystallized from methylene chloride as fine yellow needles (mp 225-226° C.).

EXAMPLE 10

Preparation of 3-acetamido-5-(4-methyl-2-nitrophenyl)-2H-pyran-2-one from 4-[3-dimethylamino-2-(4-methyl-2-nitrophenyl)-2-propen-1-ylidene]-2-methyl-2-oxazolin-5-one A suspension of 31.5 g. (100 mmol) of 4-[3-dimethylamino-2-(4-methyl-2-nitrophenyl)-2-propen-1-ylidene]-2-methyl-2-oxazolin-5-one in 90% aqueous acetic acid was stirred under a nitrogen atmosphere at 50° C. for 2.5 hours, then cooled to 5°, and filtered. The filter cake was washed with 150 ml. of cold water and dried at 60° in vacuo to yield 12.65 g. of crude product 3-acetamido-5-(4-methyl-2-nitrophenyl)-2H-pyran-2-one (mp 221-222°). After standing 2 days, the filtrate deposited an additional 0.72 g. of crude product, mp 220.5-222°. The combined crude solids were recrystallized from 67 ml. of N,N-dimethylformamide to yield 12.13 g. (42%) of 3-acetamido-5-(4-methyl-2-nitrophenyl)-2H-pyran-2-one as fine yellow needles (mp 225-226° C.).

EXAMPLE 11

Preparation of 3-acetamido-5-(2-amino-4-methylphenyl)-2H-pyran-2-one

A 500 ml. Parr bottle was charged with a solution of 14.42 g. (50 mmole) of 3-acetamido-5-(4-methyl-2-nitrophenyl)-2H-pyran-2-one in 200 ml. of N,N-dimethylformamide and 1.53 g. of 5% palladium on charcoal, and the resulting suspension shaken under hydrogen at 3 atmospheres for 18 minutes. During this time period, the theoretical (15 mmol) amount of hydrogen was absorbed. The catalyst was removed from the resulting suspension by filtration through a bed of diatomaceous earth and the filter cake was washed several times with methylene chloride. Evaporation of the solvents in vacuo yielded 13.25 g. of crude 3-acetamido-5-(2-amino-4-methylphenyl)-2H-pyran-2-one.

The analytical sample was recrystallized from methylene chloride-hexane as yellow needles (mp 214.5-215.5° C.).

EXAMPLE 12

Preparation of (E)-α-acetamido-6-methylindole-3-acrylic acid 110 ml. of 1 N sodium hydroxide were added dropwise over 30 minutes to a mixture of 26.95 g. (10.2 mmol) of crude 3-acetamido-5-(2-amino-4-methylphenyl)-2H-pyran-2-one in 200 ml. of tetrahydrofuran and 200 ml. of water under a nitrogen atmosphere. The resulting dark suspension was stirred for 30 minutes. 110 ml. of 1 N hydrochloric acid were added dropwise to the dark suspension. After removal of the tetrahydrofuran in vacuo and adjustment to pH 3, the dark suspension was cooled to 5° C., and filtered. The filter cake (21.1 g.) was dissolved in 1100 ml. of boiling methanol, treated with 2.0 g. of charcoal for 10 minutes and filtered through a bed of diatomaceous earth (which was washed with 200 ml. of hot methanol). The filtrate was concentrated to about 750 ml.; 150 ml. of water were added portionwise thereto; and the resulting solution was allowed to crystallize. A total of 16.1 g. (61%) of (E)-α-acetamido-6-methylindole-3-acrylic acid (mp 204.5-206° C.) was obtained in two crops.

The analytical sample was recrystallized from aqueous methanol as white plates, mp 207-208° C.

EXAMPLE 13

Preparation of (Z)-α-acetamido-6-methylindole-3-acrylic acid methyl ester from 3-acetamido-5-(2-amino-4-methylphenyl)-2H-pyran-2-one Approximately 10 mg. of sodium methylate were added to a stirred solution of 259 mg. (1 mmol) of 3- acetamido-5-(2-amino-4-methylphenyl)-2H-pyran-2-one in 20 ml. of methanol was added. After 18 hours, the methanol was evaporated in vacuo and the residue equilibrated between water and ethyl acetate. The organic phase was separated, dried over sodium sulfate and evaporated in vacuo to yield 197 mg. of (Z)-α-acetamido-6-methylindole-3-acrylic acid methyl ester.

EXAMPLE 14

Preparation of (E)-4-(6-methylindol-3-ylmethyene)-2-methyl-2-oxazolin-5-one from (E)-α-acetamido-6-methylindole-3-acrylic acid A suspension of 850 mg. (3.3 mmol) of (E)-α-acetamido-6-methylindole-3-acrylic acid in 20 ml. of acetic anhydride was heated at 50° C. overnight, and then evaporated in vacuo. The residue was digested with methylene chloride. Filtration and evaporation of the filtrate yielded 0.26 g. of the yellow solid product. The methylene chloride insoluble fraction was mixed with 15 ml. of acetic anhydride and heated at 50° C. overnight to yield 0.52 g. of additional methylene chloride soluble fraction, which was combined with the aforementioned product for a total of 0.77 g. of crude (E)-4-(6-methylindol-3-ylmethylene)-2-methyl-2-oxazolin-5-one.

EXAMPLE 15

Preparation of 4-[3-dimethylamino-2-(2-nitrophenyl)-2-propen-1-ylidene]-2-methyl-2-oxazolin-5-one A one-liter, 3-necked flask equipped with thermometer, stirrer, and nitrogen inlet was charged with 29.86 g. (0.255 mol) of N-acetylglycin, 82.0 g. (1 mol) of anhydrous sodium acetate, 22.0 g. (0.1 mol) of 3-dimethylamino-2-(2-nitrophenyl)acrolein, and 0.5 l. of acetic anhydride.

This mixture was stirred at room temperature (20° C.) for 15 minutes, and 18.1 ml. (0.212 mol) of acetyl chloride was added dropwise thereto over about 15 minutes. The temperature rose to 27° C., and the mixture developed a red color. After the mixture stood for about 2 hours (23° C.), an additional 18.1 ml. (0.212 mol) of acetyl chloride was added thereto over about 10 minutes. During this time the temperature rose to 33° C. The reaction was stirred for an additional 22 hours at room temperature.

Most of the acetic anhydride was removed by vacuum distillation (water aspirator) on a steam bath. 300 ml. of water and 300 ml. of ice then were added to the mixture, and after stirring for 1 hour, the resulting red suspension was extracted twice with 250 ml. of methylene chloride. Both extracts were washed in a countercurrent manner with 300 ml. of water, 500 ml. of 10% sodium bicarbonate, and 300 ml. of water. The combined organic phases were dried over sodium sulfate, filtered, and evaporated to yield 37.9 g. of a deep red solid. The residue was crystalized from 100 ml. of ethyl acetate and 25 ml. of methylene chloride cooled to −5° C. to yield 10.1 g. (33.5%) of 4-[3-dimethylamino-2-(2-nitrophenyl)-2-propen-1-ylidene]-2-methyl-2-oxazolin-5-one, m.p. 189–190° C., as a dark red solid. The mother liquor was evaporated and the residue dissolved in the minimum amount of methylene chloride, and filtered through a column of 300 g. of silica gel. This column was packed and eluted with a solution of ethyl acetate/methylene chloride (1:4). Fractions of 400 ml. were collected. Fractions 3 and 4 were evaporated (4.6 g.) and the residue recrystallized from 25 ml. of ethyl acetate to yield an additional 4.0 g. of 4-[3-dimethylamino-2-(2-nitrophenyl)-2-propen-1-ylidene]-2-methyl-2-oxazolin-5-one, m.p. 190–191°. The total yield was 14.1 g. (46.8%).

EXAMPLE 16

Preparation of (Z)-α-acetamidoindole-3-acrylic acid hydrate

A 500-ml., 3-necked round-bottom flask equipped with a mechanical stirrer, a nitrogen inlet, and a thermometer was charged with 15.8 g. (0.0524 mol) of 4-[3-dimethylamino-2-(2-nitrophenyl)-2-propen-1-ylidene]-2-methyl-2-oxazolin-5-one, 175 ml. of acetic acid, and 20 ml. (0.20 mol) of acetic anhydride. While maintaining the temperature at 15–20° C. by means of an ice bath, 15.0 g. (0.230 mol) of zinc dust was added to the flask in small portions over a period of 1.5 hours.

After stirring this mixture for 30 minutes at room temperature, 150 ml. of water and 150 ml. of ice were added thereto and the resulting mixture was stirred for 15 minutes. The contents of the flask were added to a 2 l. beaker containing 200 ml. of water and 500 ml. of methylene chloride and were briefly stirred. The resulting three-phase system was filtered and the two-phase filtrate was separated. The aqueous phase was washed with 500 ml. of methylene chloride. The methylene chloride phases were washed in a counter-current manner with 500 ml. of water. The organic phases were dried over sodium sulfate, filtered and evaporated in vacuo to yield 12.5 g. of a crude 4-(indol-3-ylmethylene)-2-methyl-2-oxazolin-5-one (5:1 parts by weight of a mixture of Z and E isomers), as a yellow solid.

The 12.5 g. of crude 4-(indol-3-ylmethylene)-2-methyl-2-oxazolin-5-one was equilibrated by heating in 200 ml. of toluene and 5 ml. of triethylamine at 85° C. for 4 hours. The suspension then was evaporated in vacuo to give 11.9 g. of 4-(indol-3-ylmethylene)-2-methyl-oxazoline-5-one (16:1 ratio of Z and E azlactones by NMR).

A suspension of the 11.9 g. of the equilibrated crude 4-(indol-3-ylmethylene)-2-methyl-2-oxazolin-one in 90 ml. of acetic acid and 10 ml. of water was stirred at room temperature for 19 hours, cooled to 5° C., and filtered. The filter cake was washed with 50 ml. of cold water (0–5° C.) and dried at 60°/ 1mm Hg for 24 hours to yield 8.7 g. (68%) of (Z)-α-acetamidoindole-3-acrylic acid hydrate, m.p. 231–232° C. An analytical sample of (Z)-α-acetamidoindole-3-acrylic acid hydrate was obtained by recrystallization from methanol-water (3:1 parts by volume) as yellow prisms, m.p. 236–236.5° C.

We claim:
1. A compound of the formula:

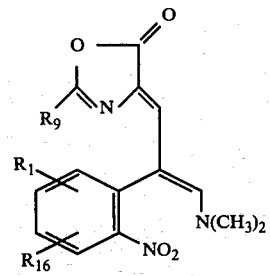

V wherein $R_1$ and $R_{16}$ individually are halogen, lower alkyl, hydroxy, lower alkoxy, aralkyloxy, amino, trihalomethyl or hydrogen and $R_9$ is lower alkyl, aryl, hydrogen or halo-lower alkyl.

2. The compound of claim 1 wherein said compound is 4-[3-dimethylamino-2-(4-methyl-2-nitrophenyl)-2-propen-1-ylidene]-2-methyl-2-oxazolin-5-one.

3. The compound of claim 1 wherein said compound is 4-[3-dimethylamino-2-(2-nitrophenyl)-2-propen-1-ylidene]-2-methyl-2-oxazolin-5-one.

* * * * *